United States Patent [19]

Matsumoto

[11] Patent Number: 5,717,205
[45] Date of Patent: Feb. 10, 1998

[54] METHOD AND APPARATUS FOR MEASURING MASS DISTRIBUTION OF A SHAFT

[75] Inventor: Norio Matsumoto, Fukushima-ken, Japan

[73] Assignee: Fujikura Rubber Ltd., Tokyo, Japan

[21] Appl. No.: 599,784

[22] Filed: Feb. 12, 1996

[30] Foreign Application Priority Data

Feb. 15, 1995 [JP] Japan ................................. 7-027068

[51] Int. Cl.$^6$ ................................................. G01N 23/02
[52] U.S. Cl. ..................... 250/306; 250/307; 250/360.1
[58] Field of Search .................................... 250/306, 307, 250/308, 358.1, 360.1

[56] References Cited

U.S. PATENT DOCUMENTS

| | | | |
|---|---|---|---|
| 3,609,368 | 9/1971 | Knorr et al. | 250/308 |
| 3,709,610 | 1/1973 | Kruegle | 356/160 |
| 3,879,608 | 4/1975 | McMullen et al. | 250/359.1 |
| 3,996,942 | 12/1976 | Baier | 131/21 R |
| 4,024,394 | 5/1977 | Reuland | 250/308 |
| 4,306,573 | 12/1981 | Rudszinat | 131/84 |
| 5,510,616 | 4/1996 | Seymour et al. | 250/308 |

*Primary Examiner*—Bruce Anderson
*Attorney, Agent, or Firm*—McCormick, Paulding & Huber

[57] ABSTRACT

A method for measuring a mass distribution of a shaft in a longitudinal axis direction thereof includes the steps of firstly, setting a plurality of measuring areas on a shaft to be measured. The measuring areas are split in the longitudinal axis direction of the shaft. Secondly, a constant amount of β rays are emitted onto each measuring area from one side of the shaft in the radial direction. The amount of β rays transmitted through the measuring areas of the shaft is measured at the other side of the shaft. Thirdly, the diameter of the shaft at each measuring area is measured to obtain a relative mass distribution of the shaft in the longitudinal axis direction in accordance with the β ray data representing the amount of β rays transmitted through each measuring area and the diameter data. A method for measuring a mass distribution of a shaft in the circumferential direction thereof is also disclosed. The invention is also directed to an apparatus for carrying out the above measuring method.

10 Claims, 7 Drawing Sheets

METHOD AND APPARATUS FOR MEASURING MASS DISTRIBUTION OF A SHAFT

BACKGROUND OF THE INVENTION

1. Field of the Invention

The present invention relates to a method and an apparatus for measuring a mass distribution of a shaft (rod or bar member) in a lengthwise direction and/or in a circumferential direction thereof.

2. Description of Related Art

To determine the properties of a golf club shaft various evaluation parameters can be used, for example, hardness, a kick point, degree of bending etc. The assignee of the present application has previously proposed (U.S. Pat. No. 5,429,008) new evaluation parameters for a golf club shaft, the first parameter being a distance $\lambda$ between a tangent line at a point on the shaft at which a predetermined load is applied to a tip portion of the shaft to deform the shaft and a point at which the tangent line intersects a neutral axis, and the second parameter being a curvature distribution $1/\rho$ of the shaft when a predetermined load is applied to a tip portion of the shaft to deform the latter.

The proposed new evaluation parameters are useful for more precisely determining the properties of a golf club shaft to thereby design and produce golf club shafts depending on the individual characteristics of a golfer.

SUMMARY OF THE INVENTION

It is an object of the present invention to provide a method and an apparatus for measuring a mass distribution of a shaft, which has been produced, so that the shaft can be evaluated from many sides, without destroying the shaft.

The mass distribution of a shaft includes a mass distribution in the axial direction and a mass distribution in the circumferential direction. If the mass distribution in the axial direction is determined, then the moment of inertia at each point of the shaft can be obtained by calculation. Moreover, if the mass distribution of the shaft is determined, the moment of inertia of a golf club having a shaft, a head attached to one end of the shaft and a grip attached to the other end of the shaft etc., can be easily calculated.

In theory, the moment of inertia can be measured by holding the shaft so as to let it swing about an optional point. Indeed, many measuring apparatuses based on this theory are marketed. However, in the known measuring apparatuses, a measurement error can be caused due to frictional resistance at the fulcrum at which the shaft is swingably supported.

When the mass distribution of a hollow shaft in the circumferential direction is measured, an irregularity in the thickness of the shaft caused upon producing the same, the presence of a void (air bubble) in the shaft, or the presence of foreign matter in the material of which the shaft is made etc., can be non-destructively detected.

According to an aspect of the present invention, there is provided a method for measuring a mass distribution of a shaft to be measured in a longitudinal axis direction thereof by setting a plurality of measuring areas on the shaft. The measuring areas are split in the longitudinal axis direction of the shaft. A constant amount of $\beta$ rays are emitted on to each measuring area from one side of the shaft in the radial direction. At the other side of the shaft the amount of $\beta$ rays transmitted through the measuring areas of the shaft is measured. Then diameter of the shaft of each measuring area is measured and in accordance with the $\beta$ ray data representing the amount of the $\beta$ rays transmitted through each measuring area and the diameter data, a relative mass distribution of the shaft in the longitudinal axis direction can be obtained.

Preferably, several measuring operations to measure the amount of transmitted $\beta$ rays are effected at different angular positions of the shaft for each measuring area, so that an average value of the measurements obtained by the measuring operations is determined to be the amount of transmitted $\beta$ rays for each measuring area.

According to another aspect of the present invention, a method for measuring a mass distribution of a hollow shaft to be measured in a circumferential direction thereof comprises the steps of firstly, inserting a $\beta$ ray sensor into a hollow portion of the hollow shaft to detect $\beta$ rays. Secondly, a constant amount of $\beta$ rays are emitted onto the hollow shaft from one side thereof in the radial direction. Thirdly, the amount of $\beta$ rays transmitted through the hollow shaft is measured at the other side of the shaft and is detected by the $\beta$ ray sensor. The hollow shaft is rotated about the longitudinal axis thereof with respect to the emittance of the $\beta$ rays, and several measuring operations are carried out at different angular positions of the hollow shaft. Fourthly, a relative mass distribution of the hollow shaft in the circumferential direction in accordance with the $\beta$ ray data representing the amount of the transmitted $\beta$ rays measured in the plural measuring operations, is obtained.

Preferably, the measuring method further comprises setting a plurality of measuring areas split in the longitudinal axis direction of the hollow shaft, wherein several measuring operations to measure the amount of $\beta$ rays transmitted are effected for each measuring area.

In a method for measuring a mass distribution of a hollow shaft in the circumferential direction, it is possible to set a plurality of measuring areas split in the axial direction of the hollow shaft, so that a plurality of $\beta$ ray measuring operations are carried out for each split measuring area.

According to another aspect of the present invention, there is provided an apparatus for measuring a mass distribution of a shaft comprising a shaft holding portion which holds a shaft to be measured. A measuring unit is provided which is relatively movable along the length of the shaft and is driven by a driving means by a predetermined displacement. A $\beta$ ray emitter and a $\beta$ ray detector are provided on opposite sides of the shaft in the measuring unit. Also provided in the measuring unit is a diameter measuring means which measures the diameter of the shaft. A measurement executing means relatively moves the measuring unit along the shaft by the driving means to obtain $\beta$ ray data representing the amount of $\beta$ rays detected by the $\beta$ ray detector and diameter data representing the diameter of the shaft detected by the diameter measuring means. A calculating means obtains a relative mass distribution of the shaft in the longitudinal axis direction thereof in accordance with a group of $\beta$ ray data and a group of diameter data.

For instance, the diameter measuring means can be comprised of a laser emitter and a light receiver provided on opposite sides of the shaft to be measured.

In the measuring apparatus, it is possible to further provide a shaft rotating mechanism which intermittently rotates the shaft held by the shaft holding portion about the longitudinal axis of the shaft by a predetermined angular displacement, so that a plurality of measuring operations for obtaining the $\beta$ ray data can be carried out at the same axial position of the shaft while rotating the shaft about the longitudinal axis thereof.

According to still another aspect of the present invention, an apparatus for measuring a mass distribution of a hollow shaft comprises a shaft holding portion which holds a hollow shaft to be measured. A β ray sensor is provided in the hollow portion of the hollow shaft along the shaft to sense the β ray. A β ray emitter is provided on one side of the hollow shaft, held by the shaft holding portion, so as to move along the hollow shaft. A β ray detector detects the β ray sensed by the β ray sensor. A shaft rotating mechanism intermittently and relatively rotates the hollow shaft, held by the shaft holding portion, and the β ray emitter by a predetermined angular displacement about the longitudinal axis of the hollow shaft. A calculating means obtains a relative mass distribution of the hollow shaft in the circumferential direction thereof at each angular position of the hollow shaft and the β ray emitter, in accordance with the β ray data obtained by the β ray detector.

The measuring apparatus can further comprise a driving means for intermittently moving the β ray emitter relative to the hollow shaft in the longitudinal axis direction of the hollow shaft by a predetermined axial displacement, so that a relative mass distribution of the hollow shaft can be obtained at each axial position of the β ray emitter.

The present disclosure relates to subject matter contained in Japanese Patent Application No. 7-27068 (filed on Feb. 15, 1995) which is expressly incorporated herein by reference in its entirety.

BRIEF DESCRIPTION OF THE DRAWINGS

The present invention will be described below in detail with reference to the accompanying drawings, in which.

DESCRIPTION OF THE PREFERRED EMBODIMENT

FIGS. 1 through 4 show an embodiment of a measuring apparatus which is adapted to measure a relative mass distribution of a hollow shaft 10 (object to be measured) in the longitudinal axis direction thereof. In the illustrated embodiment, the shaft 10 is a hollow golf club shaft whose diameter and thickness gradually vary in the longitudinal axis direction.

Figure 1:
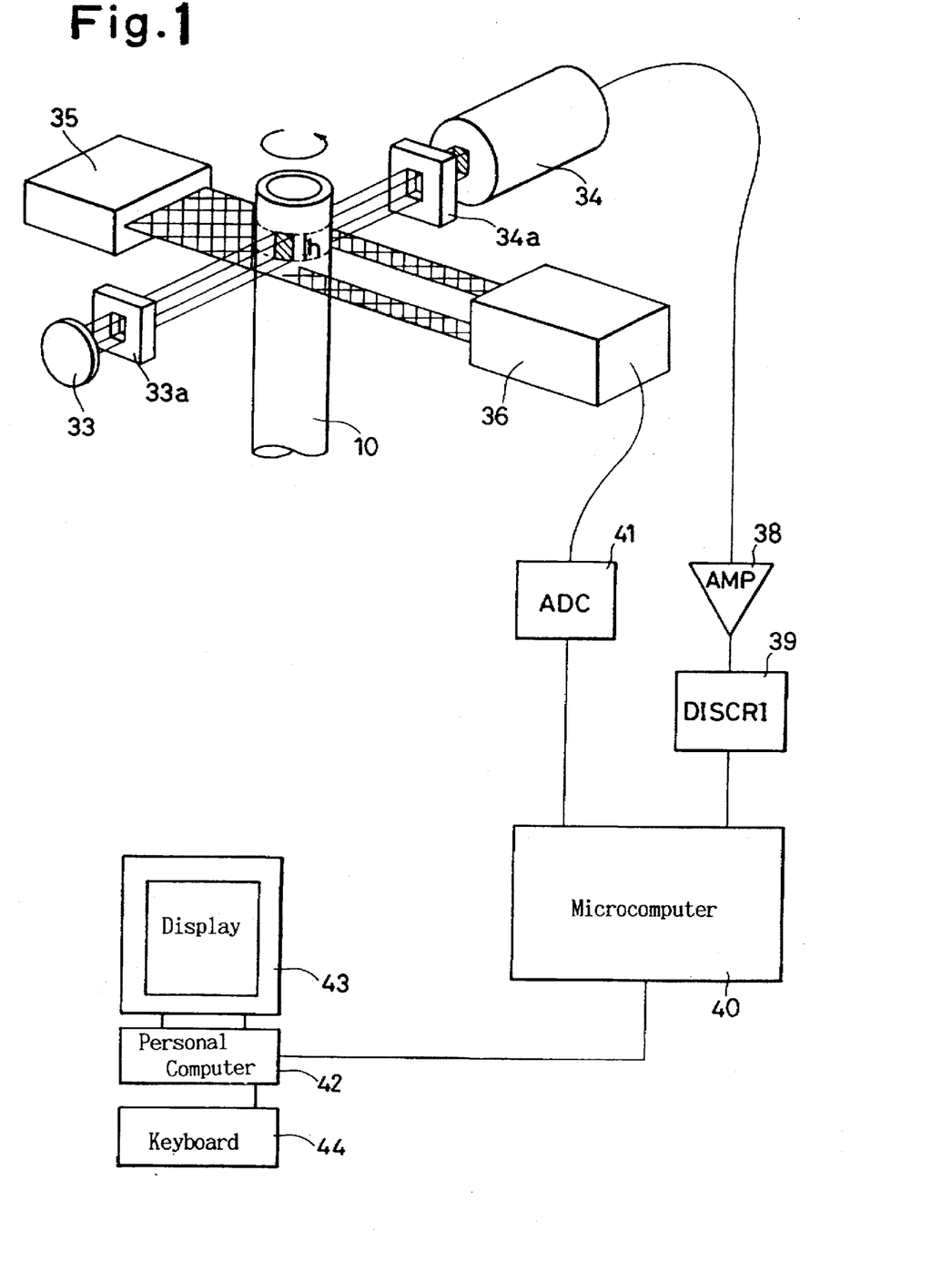
FIG. 1 is a schematic view showing the principle of measurement of a mass distribution of a shaft, according to the present invention.
Figure 2:
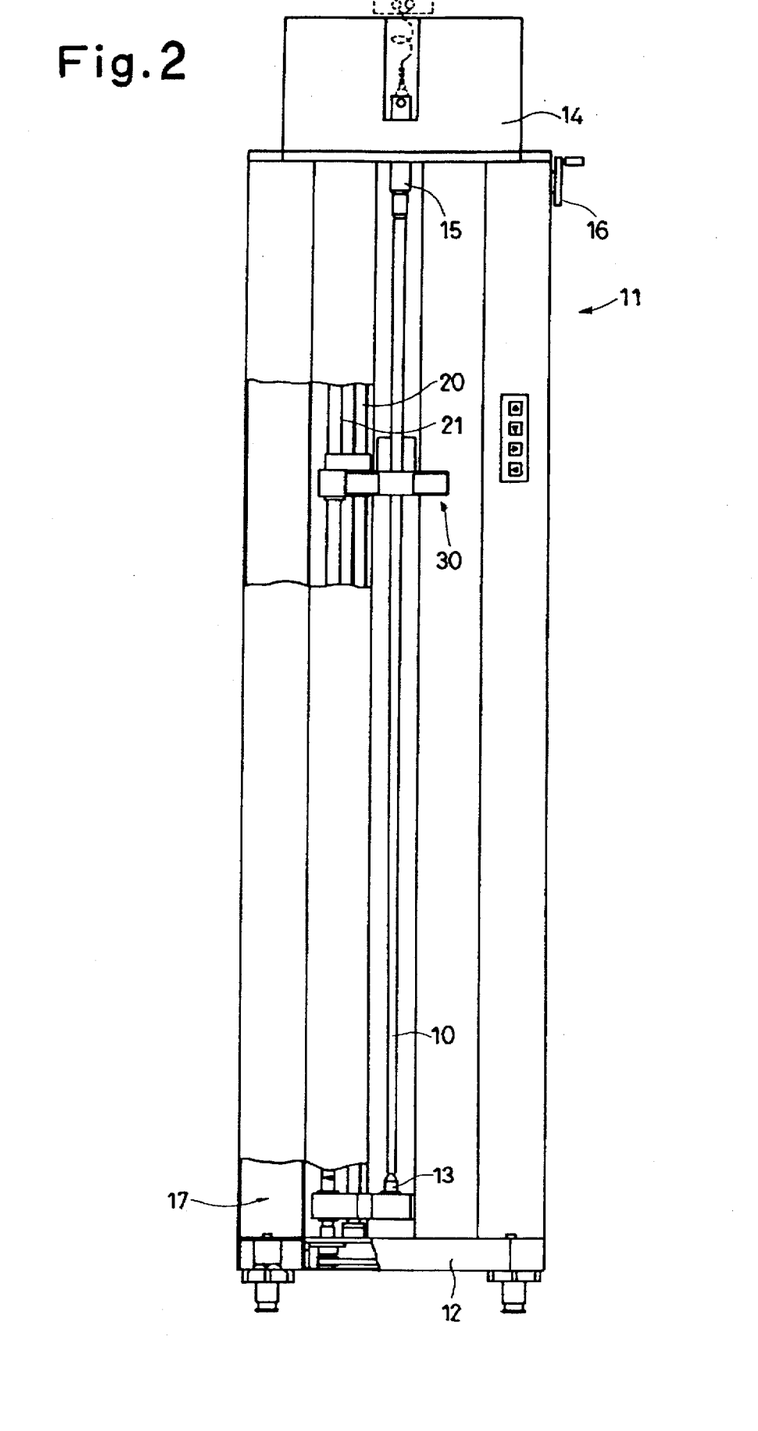
FIG. 2 is a front elevational view of a measuring apparatus shown in FIG. 1.
Figure 3:
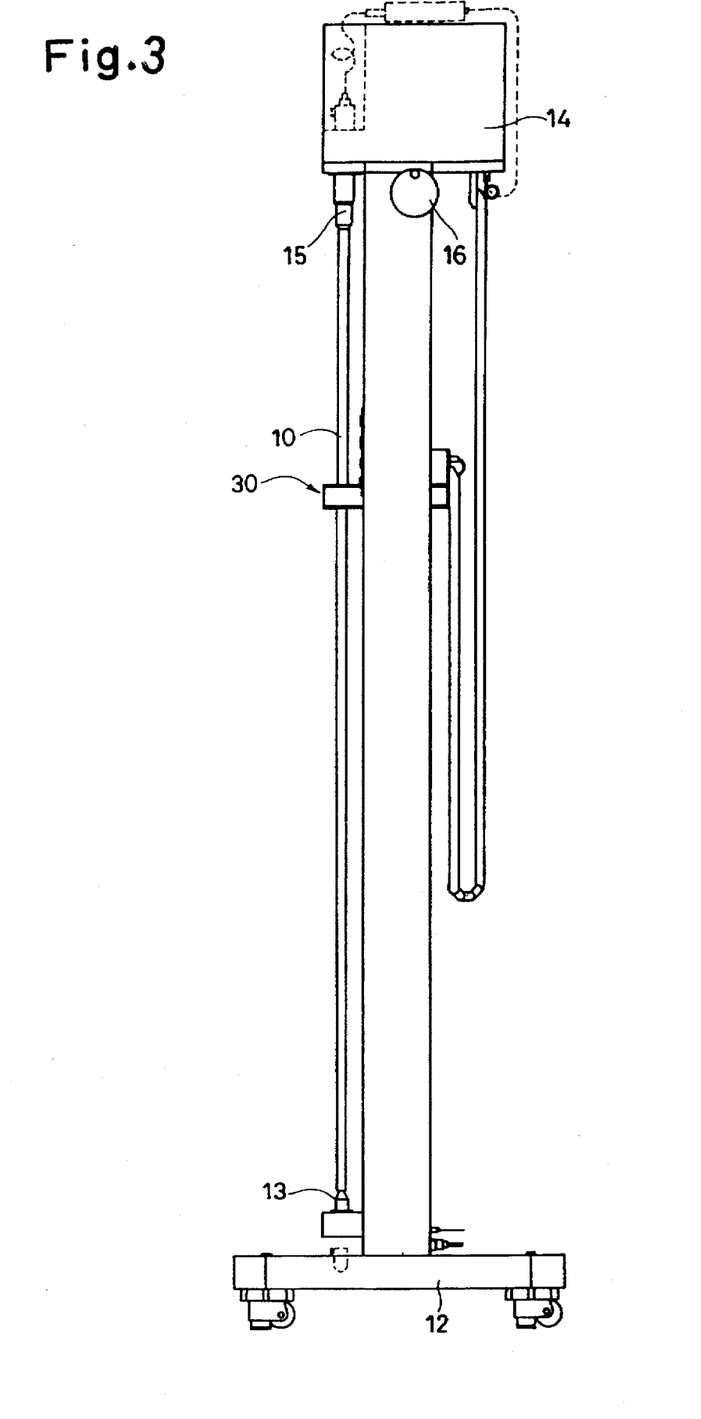
FIG. 3 is a side elevational view of the measuring apparatus shown in FIG. 2.

The measuring apparatus includes an apparatus body 11 which is provided with a lower base 12 on which a rotating vertical support shaft 13 is rotatably supported, and an upper base 14 on which an elevating vertical shaft 15, coaxial to the rotating vertical support shaft 13, is rotatably and liftably supported. The elevating vertical shaft 15 moves up or down through the rotation of an operation knob 16. The hollow shaft 10 is supported between the elevating vertical shaft 15 and the rotating vertical support shaft 13.

The rotating vertical support shaft 13 is connected to a shaft rotating mechanism 17, so that when the rotating vertical support shaft 13 is rotated by the shaft rotating mechanism 17, the hollow shaft 10, supported between the elevating vertical shaft 15 and the rotating vertical support shaft 13, is rotated together. An angular displacement of the hollow shaft 10 is detected by an encoder (not shown) provided in a drive system of the shaft rotating mechanism 17.

The apparatus body 11 is also provided with a rotatable feed screw 20 which extends in the vertical direction and a guide rail 21 which extends in a direction parallel to the feed screw 20.

An elevating measuring unit 30 is provided with a threaded portion 20a (FIG. 4) in which the feed screw 20 is screw-engaged, and a slider 21a (FIG. 4) which is slidably fitted to the guide rail 21. Consequently, when the feed screw 20 is rotated, the measuring unit 30 is moved up and down along the length of the hollow shaft 10. The position of the measuring unit 30 relative to the hollow shaft 10 in the longitudinal axis direction of the shaft is detected by an encoder (not shown) provided in a drive system for the feed screw 20.

Figure 4:
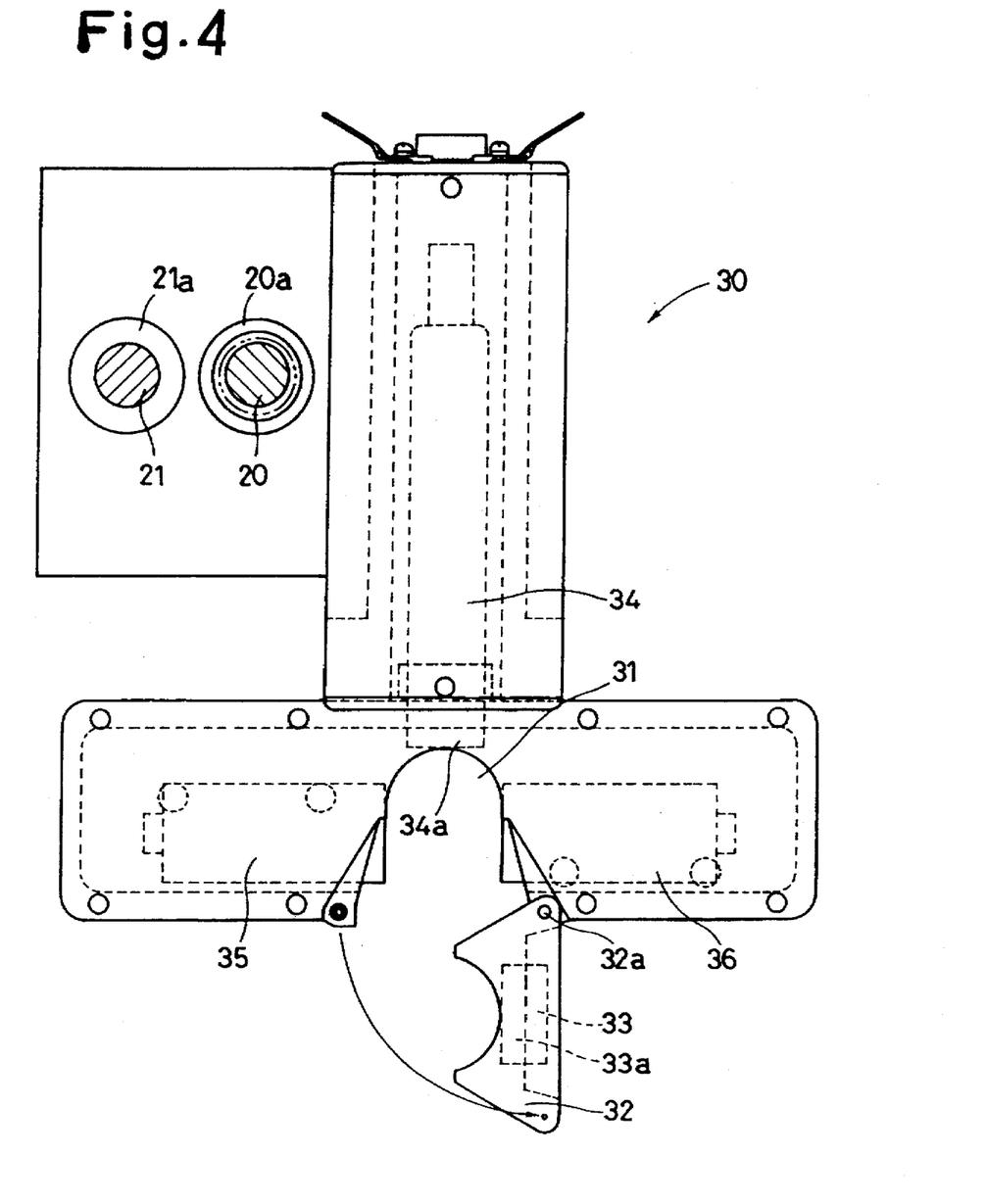
FIG. 4 is a plan view of an elevating measuring unit according to the present invention.

The measuring unit 30 is provided with a shaft insertion opening 31 which can be closed by closing a closing cover 32. The closing cover 32 is pivoted about a shaft 32a, as shown in FIG. 4. The cover 32 is provided with a β (beta) ray source 33 and a slit 33a which defines a light receiving area on the hollow shaft 10.

The measuring unit 30 is provided with a β ray detector 34 which is opposed to the β ray source 33 when the cover 32 is closed. The measuring unit 30 is also provided with a laser emitter 35 and a light receiver 36 which are positioned coaxially, perpendicular to the axis in which the β ray source 33 and the β ray detector 34 are located.

The β ray source 33 emits a predetermined amount of β rays which are transmitted through the hollow shaft 10 and received by the β ray detector 34. The laser beams emitted from the laser emitter 35 and interrupted by the hollow shaft 10 are received by the light receiver 36. In front of the β ray detector, on the light receiving side, there is a slit 34a.

The β ray is comprised of a stream of electrons or positrons, which is emitted from an atomic nucleus of a certain type of radioactive isotopic element. The level of transmission of a β ray through a substance (portion of an object to be measured) increases as the density of the substance decreases. As a consequence, the relative density of the substance can be detected by measuring the amount of β rays transmitted therethrough for a predetermined period of time.

Various detectors for detecting the β rays are known, however in the illustrated embodiment a scintillation counter using a plastic scintillator is used. Note that, scintillation is a phenomenon in which a flash of light is produced in a phosphor when struck by an ionizing photon or particle. The β rays can be effectively detected by the scintillation counter which greatly amplifies (several million times) and converts a slim fluorescent light, arising due to scintillation, into electric signals (pulse signals) using a photomultiplier tube (electron tube).

The output pulse of the β ray detector 34 is input into a microcomputer 40 through an amplifier 38 and a pulse-height discriminating/wave shaping circuit 39. The output signal of the light receiver 36 is input to the microcomputer 40 through an A/D converter 41. The light receiver 36 is comprised of a line sensor which receives the laser beams emitted from the laser emitter 35 and interrupted by the hollow shaft 10. Consequently, the diameter of the hollow shaft 10 can be detected according to data from a group of pixels of the line sensor by which the laser beams are received. The microcomputer 40 is connected to a personal computer 42, a monitoring display 43 and a keyboard 44.

Upon measurement using the measuring apparatus as constructed above, the hollow shaft 10 is held between the rotating support shaft 13 and the elevating shaft 15. The elevating measuring unit 30 is moved from either the upper or lower end of the hollow shaft 10, for example, from the upper end toward the lower end, at a predetermined pitch (by a predetermined displacement). The measurement is carried out at each height position (measuring position) corresponding to the pitch. At each measuring position, the hollow shaft 10 is rotated about the longitudinal axis thereof, so that the measurement is carried out at each angular position. Namely, a number of measurements are effected at the same height position and at different angular positions. An average value (mean value) of the measurements is obtained to increase the accuracy of the measurement. The number of measurements at each height position is appropriately determined depending on the irregularity in the thickness of the hollow shaft 10, or the purpose of the measurements, etc.

The light receiving surface area (incident height h) of the β rays emitted from the β ray source 33 is determined by the slit 33a. The β rays passing through the slit 33a are transmitted through the hollow shaft 10 before reaching the β ray detector 34 through the slit 34a. The slit 34a prevents scattered rays from entering the β ray detector 34. Namely, to eliminate measurement errors in the amount of β rays detected, due to the slit 34a only the β rays can be received by the β ray detector 34. The β rays received by the β ray detector 34 are converted into pulse signals. The number of pulses corresponds to the amount of incident rays. The pulse signals are supplied to the amplifier 38 and the pulse-height discriminating/wave shaping circuit 39 to obtain effective signals which are then input to the microcomputer 40.

The laser beams emitted from the laser emitter 35 and interrupted by the hollow shaft 10 are incident upon the light receiver 36. The analog signals output from the light receiver 36 correspond to the diameter of the hollow shaft 10 and are converted into digital signals by the A/D converter 41 and are then supplied to the microcomputer 40.

The measurement values obtained by the measuring system mentioned above are calculated using the following formulae to obtain a relative mass (weight) of the portion of the shaft (split measuring area) at the height "h", upon which the β rays are made incident.

The amount of β rays transmitted is given by:

$$I/I_0 = e^{-C \cdot p \cdot x} \quad (1)$$

wherein,

"T" (cps: count per second) represents the rate of β rays during a predetermined period of time when there is no subject (hollow shaft 10) through which the β rays are to be transmitted;

"$I_0$" (cps) represents the rate of β rays during a predetermined period of time when the β rays are transmitted through a subject (hollow shaft 10);

"C" ($cm^2/g$) represents the mass absorption coefficient;

"p" ($g/cm^3$) represents the density of the subject;

"x" (cm) represents the thickness of the subject.

The relative mass can be given by the following equations:

$$W(g) = p \cdot V \quad (2)$$

$$V(cm^3) = S \cdot x \quad (3)$$

$$S(cm^2) = h \cdot L \quad (4)$$

$$L(cm) = \pi \cdot D \quad (5)$$

wherein,

"W" represents the relative mass (weight) of the subject at the height "h";

"V" represents the volume of the subject at the height "h";

"S" represents the surface area of the subject at the height "h";

"h" represents the incident height of the β rays;

"L" represents the length of the circumference of the subject at a point at which the diameter is measured; and, "D" represents the diameter of the subject.

Note that "T" is measured in advance when no subject (hollow shaft) 10 is positioned in the measuring apparatus. The value of "T" can be obtained in accordance with the output of the β ray detector 34, and the values of "D" and "L" can be obtained in accordance with the output of the light receiver 36.

From the formula (1), we have:

$$\ln(I/I_0) = -C \cdot p \cdot x \quad p \cdot x = -\ln(I/I_0)/C \quad (6)$$

From the equations (2) and (3), we have:

$$W = p \cdot x \cdot S \quad (7)$$

From the formulae (6) and (7), we have:

$$W = -\ln(I/I_0) \cdot S/C \quad (8)$$

$$\therefore W = -\ln(I/I_0) \cdot h \cdot L/C \quad (9)$$

It should be appreciated here that the formula (9) does not include the thickness "x" of the subject. Namely, it is not necessary to measure the thickness "x". In the formula (9), the value of $\ln(I/I_0)$ is obtained from the amount of β rays transmitted, and the "h" is a constant value. The value "L" is obtained from the diameter "D" of the hollow shaft 10 which is measured by the laser emitter 35 and the light receiver 36. The value of "C" is constant on the assumption that the material of the hollow shaft 10 is uniform.

As a consequence, the relative mass distribution of the hollow shaft 10 can be measured by repeatedly carrying out the measuring operations mentioned above throughout the whole length of the hollow shaft 10, while moving the elevating measuring unit 30 at a pitch corresponding to the height "h" in the direction of the length of the hollow shaft 10. Since the total weight of the hollow shaft 10 is measured in advance, assuming that the total weight is proportionally distributed to the split measuring areas in accordance with the relative mass distribution, the mass for each split measuring area can be obtained. The incidence height "h" of the β rays can be varied by varying the height of the slits 33a and 34a. The measuring areas can be split more finely by setting the height "h" to be a smaller value to thereby change the pitch of the movement (each displacement) of the measuring unit accordingly.

Table 1 below shows examples of actual measurement data of the β rays. In the experiments, for the purpose of simplification, one measuring operation was carried out for each split measuring area. If a plurality of measuring operations are effected at different angular phases for the same split measuring area, average values of the measurements (counted values of the transmitted β rays and the measured diameters) can be used. In Table 1, "h" was 20 mm. The distance (mm) represents the position of the center of the height "h". The measuring time for each split measuring area was 20 seconds, and the total weight of the shaft was 96.0 g.

TABLE 1

| No. | distance (mm) | angle (°) | count (C) | mean count (C) | mean diameter (mm) | mass (g) |
|---|---|---|---|---|---|---|
| 1 | 10 | 0 | 702 | 702.00 | 15.93 | 2.06 |
| 2 | 30 | 0 | 911 | 911.00 | 15.77 | 2.08 |
| 3 | 50 | 0 | 838 | 838.00 | 15.63 | 2.12 |
| 4 | 70 | 0 | 780 | 780.00 | 15.55 | 2.16 |
| . | . | . | . | . | . | . |
| . | . | . | . | . | . | . |
| . | . | . | . | . | . | . |
| 55 | 1090 | 0 | 288 | 288.00 | 8.79 | 1.62 |
| 56 | 1110 | 0 | 294 | 294.00 | 8.85 | 1.62 |
| 57 | 1130 | 0 | 261 | 261.00 | 8.91 | 2.44 |

Figure 5:
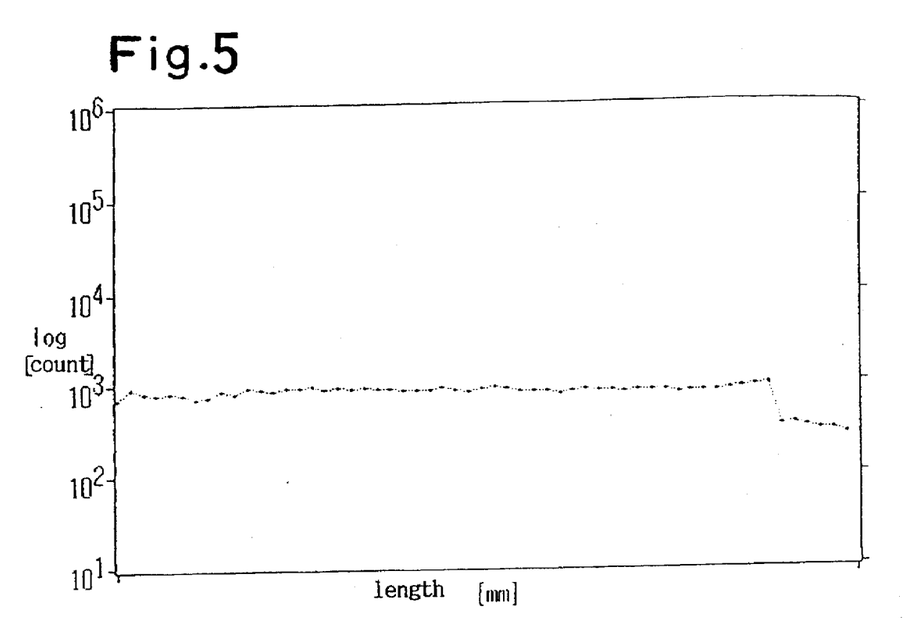
FIG. 5 is a graph showing plotted measurement data of a β ray.
Figure 6:
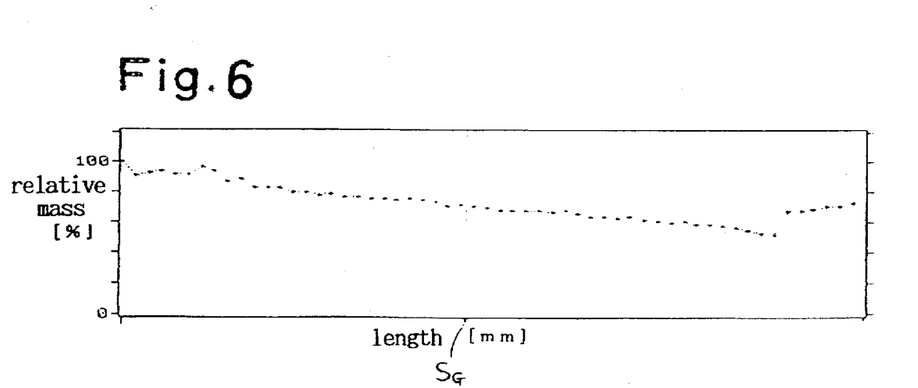
FIG. 6 is a graph of a mass distribution obtained from the measurement data shown in FIG. 5.

FIG. 5 shows a graph obtained by plotting the measurement data shown in Table 1. It can be seen from FIG. 5 and Table 1 that the number counted at the front portion of the shaft is relatively small. Namely, it can be understood that the front portion of the shaft has a high relative density. This is because there is a reinforcing rod inserted in the front end of the hollow shaft 10. FIG. 6 shows a relative mass distribution curve which is obtained by proportionally distributing the total weight of the hollow shaft 10 to each split measuring area in accordance with the relative mass distribution.

As can be seen from the foregoing, the mass distribution of the hollow shaft 10 can be measured without any destruction to the shaft. In accordance with the mass distribution curve thus obtained, the center of gravity, the moment of inertia about the center of gravity, and the moment of inertia about an optional point etc., of the hollow shaft 10 can be calculated.

One of the most significant advantages of the present invention is that when the hollow shaft 10 is cut at an optional length, the associated values at the length can be similarly obtained in the calculation mentioned above. Specifically, if the total mass distribution curve for one hollow shaft 10 is determined, a mass distribution curve at an optional length thereof can be easily obtained by a computer. Consequently, the weight and the mass distribution can be obtained in accordance with the mass distribution curve at the length at which the hollow shaft 10 is cut. In the production of a golf club, the hollow shaft 10 must be cut at an appropriate length. In the present invention, a mass distribution of a golf club shaft which is obtained by cutting the hollow shaft 10 whose weight distribution has been determined at an optional length can be obtained by calculation.

The arithmetic operation in the present invention will be discussed below.

Figure 7:
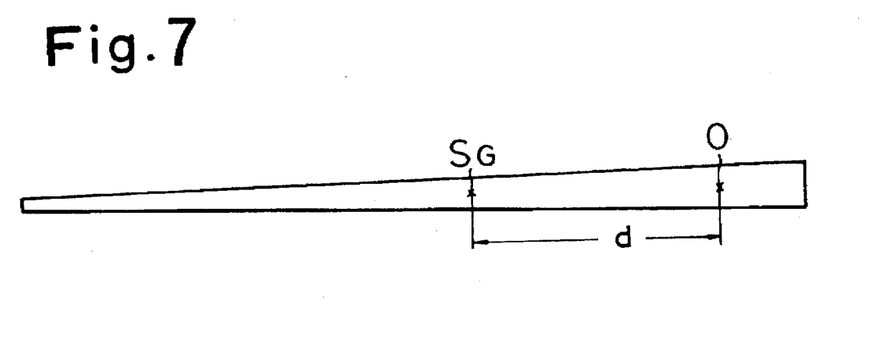
FIG. 7 is an explanatory view showing the moment of inertia about an optional point of a shaft.

The center of gravity $S_G$ of the hollow shaft 10 corresponds to a position with respect to which the surface areas of the right and left portions in the mass distribution curve shown in FIG. 6 are identical. The moment of inertia $I_{SG}$ about the center of gravity $S_G$ is given as an integral value of the product of the distance between the center of the split measuring area and the center of gravity and the weight of the split measuring area. Also, as can be seen in FIG. 7, a moment of inertia $I_{SO}$ about a point located at a distance "d" from the center of gravity $S_G$ is given by:

$$I_{SO}=I_{SG}+M \cdot d^2$$

wherein M designates the total weight of the hollow shaft 10.

If $I_{SO}$ is a large value, the hollow shaft 10 tends not to move, but once it moves, it is difficult for the hollow shaft to stop moving. Conversely, if the value of $I_{SO}$ is small, the hollow shaft 10 can be easily moved and stopped.

The necessary values (weights and positions, etc.) of a head, a grip, an adhesive, or a tape, etc., that are attached or applied to the hollow shaft 10 to produce a golf club can be also easily calculated.

Figure 8:
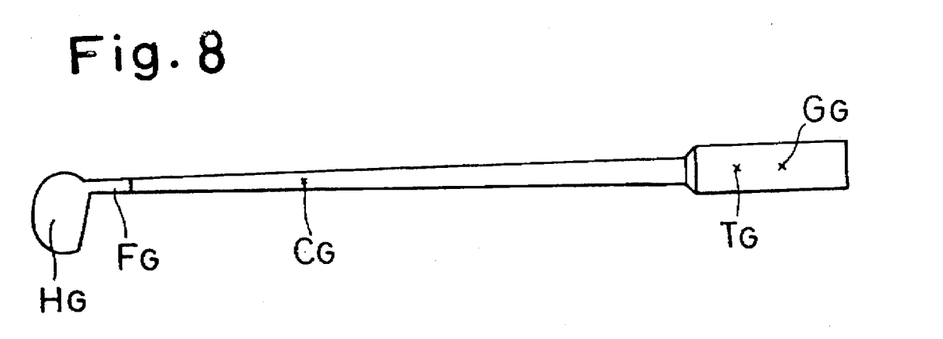
FIG. 8 is a schematic view of main components of a golf club shaft and a center of gravity of each component, by way of example.

FIG. 8 shows examples of the centers of gravity of the main components of a golf club, which are taken into account to obtain the moment of inertia $I_{CG}$ of the golf club. In FIG. 8, "$C_G$" designates the center of gravity of the golf club, "$H_G$" the center of gravity of the head, "$F_G$" the center of gravity of the ferrule and the adhesive, "$G_G$" the center of gravity of the grip, and "$T_G$" the center of gravity of the tape wound around the shaft and underneath the grip, respectively.

The moment of inertia of a golf club (finished product) about an optional point can be calculated, taking into account the center of gravity and the weight, of the golf club components and those of the hollow shaft 10 which is cut at an appropriate length.

Figure 9:
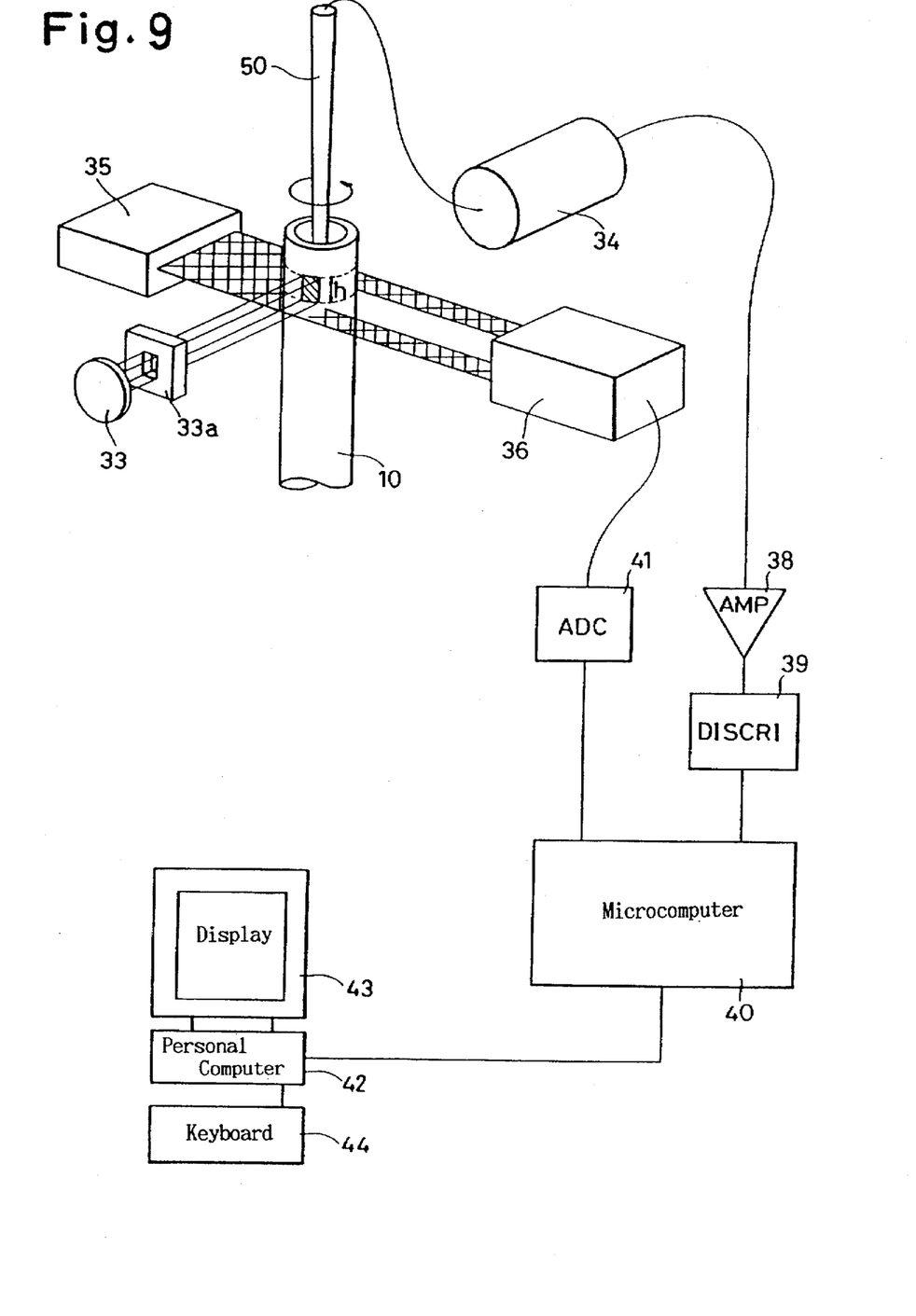
FIG. 9 is a schematic view of a measuring system to measure a mass distribution of a hollow shaft in the circumferential direction; and, FIG. 10 is a schematic sectional view of a defective portion found by the measurement of a mass distribution in the circumferential direction, by way of example.

FIG. 9 shows an embodiment in which the present invention is applied to a measuring apparatus which measures a relative mass distribution of a hollow shaft in the circumferential direction. In this embodiment, a β ray sensor 50 is inserted in the hollow shaft 10 and is connected to the β ray detector 34, shown in FIGS. 1 through 4. The β rays emitted from the β ray emitter 33 and transmitted through the hollow shaft 10 are detected (counted) by the β ray detector 34 through the β ray sensor 50. The sensor is comprised of a certain kind of optical fiber which receives the β rays emitted from the β ray emitter 33 and transmitted through the wall surface of the hollow shaft 10 toward the center of the hollow shaft 10 to effectively make the β rays incident upon the β ray detector 34 without leakage.

In the embodiment illustrated in FIG. 9, the hollow shaft 10 is intermittently rotated at a predetermined angular pitch in each split measuring area. Namely, a plurality of measuring operations (preferably more than two measuring operations) are carried out for each split measuring area in the longitudinal axis direction of the hollow shaft 10.

Figure 10:
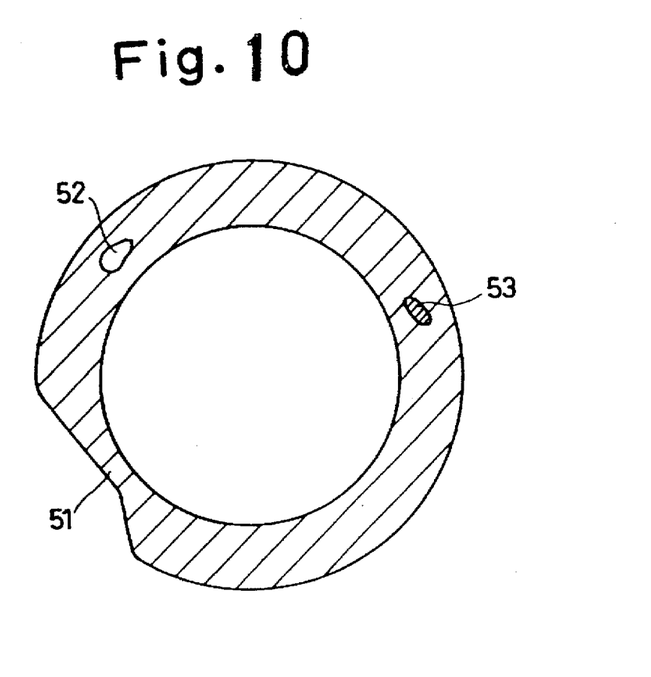

FIG. 10 schematically shows the four measuring operations carried out for the hollow shaft 10 which is intermittently rotated at an angular pitch of 90° in a split measuring area. If the hollow shaft 10 has a void (air bubble) 52 or an irregular thickness portion 51 or contains a foreign matter 53 whose density is different from the density of the remaining portion of the shaft, the number of β rays counted at the measuring angular positions are not identical. Thus, flaws can be non-destructively detected. If the measuring areas are split more finely in the circumferential direction, a more precise mass distribution can be obtained and different kinds of flaws can be correctly detected.

If the embodiment illustrated in FIG. 9 is adapted to measure the mass distribution in the circumferential direction only of a specific portion of the hollow shaft 10, it is not necessary to set a plurality of split measuring areas in the longitudinal axis direction of the hollow shaft 10.

Although the subject to be measured is the hollow shaft 10 in the illustrated embodiments, the present invention can be equally applied to a measurement of a mass distribution in the longitudinal axis direction of a solid shaft. Moreover, the present invention can be adapted to analyze the properties of any shaft, such as, a ski stick or a pole for the pole vault etc.

What is claimed is:

1. A method for measuring a mass distribution of a shaft to be measured in a longitudinal axis direction thereof, comprising steps of:

setting a plurality of measuring areas, split in the longitudinal axis direction of the shaft, on the shaft;

emitting a same amount of $\beta$ rays onto each said measuring area from one side of said shaft in the radial direction and measuring the amount of $\beta$ rays transmitted through said measuring areas of said shaft at the other side of the shaft;

measuring the diameter of the shaft at each measuring area; and obtaining a relative mass distribution of the shaft in the longitudinal axis direction in accordance with the $\beta$ ray data, representing the amount of the $\beta$ rays transmitted through each measuring area, and the diameter data.

2. The method for measuring a mass distribution of a shaft according to claim 1, wherein a plurality of measuring operations, to measure the amount of transmitted $\beta$ rays, are effected at different angular positions of the shaft for each measuring area, so that an average value of the measurements obtained by the plural measuring operations is determined to be the amount of the transmitted $\beta$ rays for each measuring area.

3. A method for measuring a mass distribution of a hollow shaft to be measured in a circumferential direction thereof, comprising steps of:

inserting a $\beta$ ray sensor in a hollow portion of the hollow shaft to detect $\beta$ rays;

emitting the same amount of $\beta$ rays onto the hollow shaft from one side thereof in a radial direction and measuring the amount of $\beta$ rays transmitted through the hollow shaft detected by the $\beta$ ray sensor, wherein a plurality of measuring operations are carried out at different angular positions of the hollow shaft with respect to said radial direction of $\beta$ ray emitting and to which different angular positions said hollow shaft is brought by rotation about the longitudinal axis of said hollow shaft; and obtaining a relative mass distribution of the hollow shaft in the circumferential direction in accordance with the $\beta$ ray data representing the amount of the transmitted $\beta$ rays measured in said plurality of measuring operations.

4. The method for measuring a mass distribution of a hollow shaft according to claim 3, further comprising setting a plurality of measuring areas split in the longitudinal axis direction of the hollow shaft on the shaft, and wherein a plurality of measuring operations are carried out at different angular positions of said shaft, to measure the amount of the transmitted $\beta$ rays, for each of said measuring areas.

5. A method for measuring a mass distribution of a hollow shaft according to claim 4, further comprising the steps of:

measuring a diameter of the shaft at each of said measuring areas; and processing said measured amounts of transmitted $\beta$ rays and said measured diameters of said hollow shaft at said measuring areas to obtain a relative mass distribution of the hollow shaft and to detect flaws in said hollow shaft in the longitudinal direction of said shaft.

6. An apparatus for measuring a mass distribution of a shaft, comprising:

a shaft holder which holds a shaft to be measured;

a measuring unit which is relatively movable along the length of the shaft;

driving means for intermittently moving the measuring unit relative to the shaft along the length of the shaft by a predetermined displacement;

a $\beta$ ray emitter and a $\beta$ ray detector, both provided in the measuring unit, said $\beta$ ray emitter and $\beta$ ray detector being positioned on opposite sides of the shaft;

diameter measuring means provided in the measuring unit for measuring the diameter of the shaft;

measurement executing means for relatively moving the measuring unit along the shaft by the driving means to obtain $\beta$ ray data representing the amount of $\beta$ rays detected by the $\beta$ ray detector and diameter data representing the diameter of the shaft detected by the diameter measuring means; and, calculating means for obtaining a relative mass distribution of the shaft in the longitudinal axis direction thereof in accordance with a group of $\beta$ ray data and a group of diameter data.

7. The apparatus for measuring a mass distribution of a shaft according to claim 6, further comprising a shaft rotating mechanism which intermittently rotates the shaft held by the shaft holding portion about the longitudinal axis of the shaft by a predetermined angular displacement, so that a plurality of measuring operations to obtain the $\beta$ ray data can be carried out at the same axial position of the shaft while rotating the shaft about the longitudinal axis thereof.

8. The apparatus for measuring a mass distribution of a shaft according to claim 6, wherein said diameter measuring means comprises a laser emitter and a light receiver positioned on opposite sides of the shaft to be measured.

9. An apparatus for measuring a mass distribution of a hollow shaft, comprising:

a shaft holder which holds a hollow shaft to be measured;

a $\beta$ ray sensor which is provided in the hollow portion of the hollow shaft along the shaft to sense the $\beta$ ray;

a $\beta$ ray emitter provided on one side of the hollow shaft held by the shaft holder so as to move along the hollow shaft;

a $\beta$ ray detector which detects the $\beta$ ray sensed by the $\beta$ ray sensor;

a shaft rotating mechanism which intermittently and relatively rotates the hollow shaft held by the shaft holder and the $\beta$ ray emitter by a predetermined angular displacement about the longitudinal axis of the hollow shaft; and calculating means for obtaining a relative mass distribution of the hollow shaft in the circumferential direction thereof at each angular position of the hollow shaft and the $\beta$ ray emitter in accordance with the $\beta$ ray data obtained by the $\beta$ ray detector.

10. The apparatus for measuring a mass distribution of a shaft according to claim 9, further comprising a driving means for intermittently moving the $\beta$ ray emitter relative to the hollow shaft in the longitudinal axis direction of the hollow shaft by a predetermined axial displacement, so that a relative mass distribution of the hollow shaft can be obtained at each axial position of the $\beta$ ray emitter.

* * * * *